(12) United States Patent
Isogai et al.

(10) Patent No.: US 7,404,312 B2
(45) Date of Patent: Jul. 29, 2008

(54) HUMIDITY-SENSITIVE ELEMENT FOR HUMIDITY SENSOR

(75) Inventors: Toshiki Isogai, Nagoya (JP); Takahiko Yoshida, Okazaki (JP); Inao Toyoda, Anjo (JP)

(73) Assignees: Nippon Soken, Inc., Nishio (JP); DENSO CORPORATION, Kariya (JP)

( * ) Notice: Subject to any disclaimer, the term of this patent is extended or adjusted under 35 U.S.C. 154(b) by 348 days.

(21) Appl. No.: 10/864,361

(22) Filed: Jun. 10, 2004

(65) Prior Publication Data

US 2004/0254306 A1  Dec. 16, 2004

(30) Foreign Application Priority Data

Jun. 12, 2003  (JP)  ............................. 2003-168034

(51) Int. Cl.
*G01N 7/00* (2006.01)
(52) U.S. Cl. .................. 73/29.01; 73/29.02; 73/335.02; 73/335.04
(58) Field of Classification Search ................ 73/29.01, 73/29.02, 335.02, 335.04
See application file for complete search history.

(56) References Cited

U.S. PATENT DOCUMENTS

| 5,011,905 A | 4/1991 | Lubowitz et al. |
| 5,161,085 A | 11/1992 | Sakai et al. |
| 6,262,223 B1 * | 7/2001 | Meador et al. ............... 528/353 |

FOREIGN PATENT DOCUMENTS

| JP | B-2827199 | 9/1988 |
| JP | B-2529136 | 6/1996 |
| JP | A-H11-56654 | 6/1999 |
| JP | 2002-005867 | 1/2002 |
| JP | A-2002-005867 | 1/2002 |
| JP | 2003-232765 | 8/2003 |
| JP | 2006-119153 | 5/2006 |
| WO | WO 01/69225 | 9/2001 |

* cited by examiner

*Primary Examiner*—Ana L Woodward
(74) *Attorney, Agent, or Firm*—Posz Law Group, PLC

(57) ABSTRACT

The invention provides a humidity-sensitive element using, as a humidity-sensitive film, a polyimide having a molecular structure capable of forming a network structure at a high density, exhibiting less drift after being left standing at a high temperature and a high humidity and having excellent characteristics. A humidity-sensitive element according to the invention uses the polyimide obtained by dehydrating and ring closing a polyamide acid forming a network structure in which terminals of basic molecular chains are interconnected with one another, as a humidity-sensitive film. The humidity-sensitive element of the invention suitably uses a polyimide, in which terminals of basic molecular chains are interconnected with one another by use of triamine or a tricarboxylic acid, as a humidity sensitive film.

13 Claims, 2 Drawing Sheets

Z: ―[ACID COMPONENT―DIAMINE COMPONENT]$_n$ ACID COMPONENT―

HUMIDITY-SENSITIVE ELEMENT FOR HUMIDITY SENSOR

BACKGROUND OF THE INVENTION

1. Field of the Invention

This invention relates to a humidity-sensitive element using a polyimide film as a humidity-sensitive film.

2. Description of the Related Art

A humidity sensor converts a change resulting from humidity and moisture to an electric quantity and executes signal processing by use of an electronic circuit. It has been widely employed to satisfy a demand for humidity control in a variety of objects. Among humidity sensors, a polymer humidity sensor that utilizes a change of an electric characteristic of a polymer material, such as an electric resistance or a dielectric constant, with absorption and desorption of water, is known. An electrostatic capacitance type, as one such sensor utilizes the phenomenon that a composite dielectric constant of a polymer increases when moisture is absorbed, and detects this phenomenon as a capacitance change between electrodes.

A large number of humidity sensors using polyimide, as a humidity-sensitive film in a humidity sensitive element for a humidity sensor, have been reported in the past. However, these humidity sensors have a water absorption ratio as great as 1 to 3% and involve the problem of a drift of quality when they are left standing at a high temperature and a high humidity. This drift of quality presumably results from the increase of the water absorption ratio due to hydrolysis and swelling of the polyimide. To reduce the drift, therefore, a method for reducing the water absorption ratio has been proposed (for example, refer to Japanese Patent No. 2,529,136).

This method suppresses the increase of the water absorption ratio by adding fluorine and increasing the hydrophobicity. However, because of the high hydrophobicity resulting from fluorine, the water absorption ratio itself drops and the drop in sensitivity becomes remarkable. A biphenyltetracarboxylic acid type polyimide (for example, U-varnish S or A, product of Ube Kosan K. K.) is known as a polyimide having a low water absorption ratio. Because this polyimide has a property such that it undergoes laminar orientation, from the aspect of a molecular structure, water absorption among the molecules can be suppressed. When experiments are carried out by using this polyimide for the humidity sensitive film, the tendency that the drift under a high temperature high humidity condition is small at the initial stage, and the effect of the low water absorption ratio, can be observed but, after a while, the drift gradually takes place. The reason is presumably because the clearances among the molecules are expanded due to swelling under a high temperature high humidity condition with the result of an increase of the water absorption ratio. Therefore, the present inventor has previously proposed a molecular structure for forming a network structure by coupling the polyimide molecules with one another to suppress the volume change due to swelling that occurs when the absorbed water undergoes aggregation (Japanese Unexamined Patent Publication (Kokai) No. 2003-232765).

However, this humidity sensitive element cannot sufficiently suppress the drift when it is left standing in a high temperature high humidity atmosphere of 65° C. and 90% RH, for example. In the film formation process of the polyimide of this humidity sensitive element, a polyamide acid, the terminals of which are terminated with acetylene, is heat-treated. Therefore, three acetylenes at the terminals react with one another during hardening and form a benzene ring, and the network structure is thus formed. Because the imidation reaction due to dehydration and ring closure of the polyamide acid occur simultaneously at this time, the reaction ratio of the formation of the benzene rings is presumably about 30%. Therefore, the network structure cannot be formed in a sufficient density and the effect of suppressing the drift is believed to be small.

The invention solves the problems described above by using a polyimide having a molecular structure capable of forming a network structure at a high density as a humidity sensitive film, and provides a humidity sensitive element having a small drift after being left standing at a high temperature and a high humidity but excellent characteristics.

SUMMARY OF THE INVENTION

To form a network structure at a higher density than in the prior art method, the invention is specifically based on the concept that the reaction for forming the network structure and the dehydration ring closing reaction of an amide acid are separated from each other, and solves the problems described above by changing the molecular structure for forming the network structure from a structure in which the terminals are terminated by acetylene to a structure in which the molecular chains are coupled with one another by triamine or tricarboxylic acid which are capable of reacting at a lower temperature than the dehydration ring closing reaction of the amide acid.

In other words, the humidity sensitive element according to the invention uses, as a humidity-sensitive film, a polyimide obtained by dehydrating and ring closing a polyamide acid having a network structure in which terminals of basic molecular chains are interconnected with one another.

The first preferred form of the basic molecular chain has a molecular structure expressed by the following formula (1):

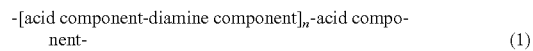

(where n is a number of repetitions representing a degree of polymerization).

Preferably, the humidity sensitive element according to the invention uses, as a humidity sensitive film, a polyimide in which the terminals of the basic molecular chains having the molecular structure expressed by the formula (1) are interconnected by use of triamines. Suitable examples of the triamine are 2,4,6-triaminopyridine and 1,3,5-triaminobenzene.

The number of repetitions of the polyamide acid in the formula (1) is generally from 1 to 30. The density of the network structure contained in a unit volume can be changed by selecting this repetition number of the polyamide acid. When the network structure is excessively increased by decreasing the number of repetitions, however, the residual stress and the hardness of the film become greater and cracking and peeling are likely to occur. Therefore, it is preferred to obtain a film having suitable properties by adjusting a blend ratio of starting monomers (diamine and diacid anhydride) so that the number of repetitions becomes from about 3 to about 20 during synthesis of the polyamide acid.

In the second preferred form as the basic molecular chain, the basic molecular chain has a molecular structure expressed by the following formula (2):

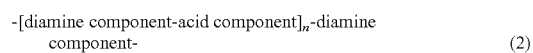

(where n is a number of repetitions representing a degree of polymerization).

Preferably, a polyimide in which the terminals of the basic molecular chains having the molecular structure expressed by this formula (2) are interconnected by a tricarboxylic acid is used as the humidity sensitive film. A preferred example of the tricarboxylic acid is trimesic acid or trimesitinic acid.

The number of repetitions n in the formula (2) described above is generally from 1 to 30, preferably from 3 to 20, in the same way as in the formula (1).

The network structure in the invention generally assumes a hexagonal network but is not limited thereto.

The acid component and the diamine component in the formulas (1) and (2) described above are not limited, in particular, and contain those which originate from acid anhydrides and diamines used for polycondensation of the polyimide. A preferred acid component has a molecular weight expressed by the formula (3):

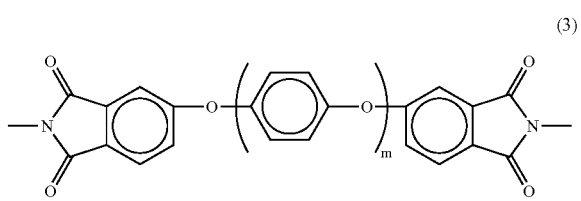

(3)

(where m is an integer of 0 to 5).

In the formula (3) given above, at least a part of an ether bond (—O—) may suitably be substituted by a thioether bond (—S—). A preferred diamine component has a molecular structure expressed by the formula (4):

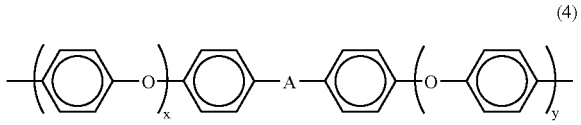

(4)

(where A is a single bond, a polyfluoroalkyl group or a sulfonyl group, m is an integer of 0 to 5 and each of x and y is an integer of 1 to 5). A lower alkyl group having 1 to 6, preferably 1 to 3, carbon atoms is selected as the alkyl of the polyfluoroalkyl group described above. From the aspects of production and performance, m is preferably 0 to 2 and x and y are preferably from 1 to 3.

In the invention, a particularly preferred molecular chain has a molecular structure expressed by the formula (5):

the polyamide acid having the network structure in which the terminals are interconnected with one another as the humidity sensitive film.

DESCRIPTION OF THE PREFERRED EMBODIMENTS

Figure 1:
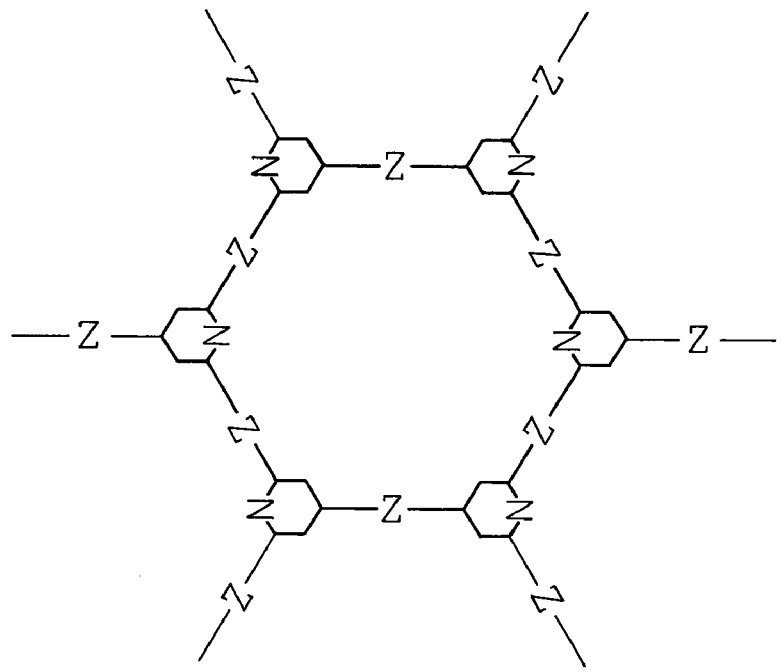
FIG. 1 shows an example of a molecular structure of polyimide according to the invention.

FIG. 1 shows an example of a molecular structure of polyimide according to the invention. Molecular chains as a basic structure represented by the formula (1) couple with one another through triaminopyridine reacting at normal temperature and form a network structure. The polyimide is generally obtained by heating a polyamide acid under the state where it is dissolved in a solvent such as an NMP (N-methylpyrrolidone) solution and then imidizing the heated product. The polyimide of the invention can be obtained by reacting triaminopyridine with a polyamide acid of a polyimide precursor having acid anhydrides at both terminals. In other words, this reaction between the polyamide acid and triaminopyridine is the amidation reaction between the acid anhydride and amine, and can be obtained by mixing triaminopyridine with the polyamide acid solution at room temperature. The network structure can be formed in this way before the polyamide acid is hardened by heat-treatment. In comparison with the case where both terminals described above are acetylene, the effect of suppressing a drift is believed higher because the density of the network structure becomes higher.

Next, a production method of the humidity sensor will be explained. First, a film of a lower electrode is formed on a silicon substrate. A material that does not easily undergo

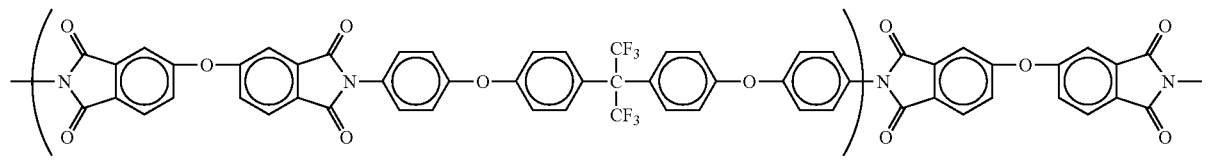

(5)

(where n is a number of repetitions representing a degree of polymerization).

In the invention, a humidity sensor can be acquired by using the humidity sensitive element described above.

In the humidity sensitive element according to the invention, the drift occurring when the element is left standing at a high temperature and a high humidity can be suppressed by using the polyimide obtained by dehydrating and ring closing oxidation and corrosion such as Au is preferred as an electrode material. It is possible to use Pt, Cr, and the like besides Au. The thickness of the film is about 200 nm, for example. The lower electrode is then patterned with photolithography.

Next, a humidity sensitive film of polyimide is formed. A formation method of the film uniformly applies a polyamide acid solution as a precursor of the polyimide onto the substrate by spin coating. Dehydration and polymerization are thereafter carried out inside an oven, etc, to form the polyimide. The polyimide is patterned by photolithography, dry etching or printing.

An upper electrode is formed next. This upper electrode is preferably formed of a material that does not easily undergo oxidation and corrosion due to absorption of humidity in the same way as in the case of the lower electrode. The upper electrode must have the function of water permeability and its film thickness must be as thin as from about 10 to about 50 nm, for example. It is advisable at this time to form the film, while only desired portions of the substrate are kept open in advance, by use of a metal mask, etc.

Figure 2:
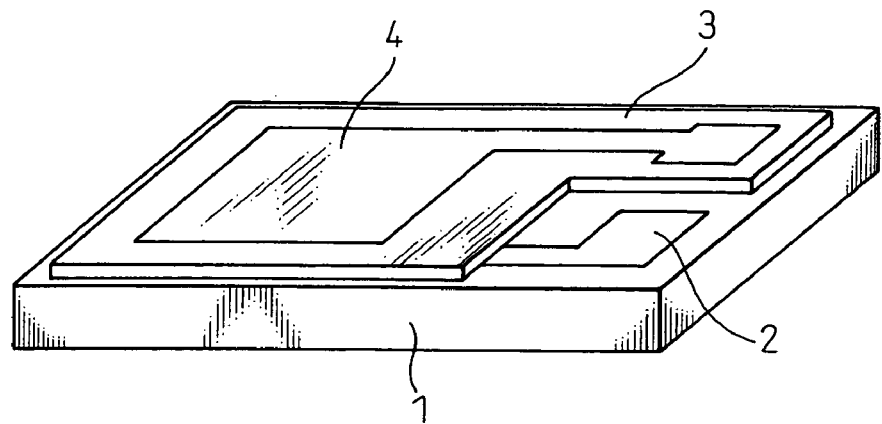
FIG. 2 is a schematic view showing an example of a humidity sensor using a humidity sensitive film according to the invention.

Finally, dicing is carried out to complete the sensor. FIG. 2 shows a perspective view of the sensor.

Another example of the production method first forms a pair of opposing comb-tooth electrodes for the lower electrode and forms the polyimide humidity sensitive film on the lower electrode, and the production method is not limited. The sensor of this embodiment has been explained regarding the characteristics of an electrostatic capacity type but the invention can be similarly applied to other types such as a resistance type, an oscillation frequency change type of a quartz oscillator, etc, and is not limited to.

Embodiments of the invention will be hereinafter explained in detail with reference to the drawings. FIG. 1 shows an example of a molecular structure of the humidity sensitive element according to the invention. To form a film having this molecular structure, triaminopyridine is stirred and reacted at normal temperature with a polyamide acid, represented by the formula (5) (n=1), the terminals of which are terminated with a diacid anhydride, in a solvent so as to couple the molecular chains with one another. Because the molecular chains couple with one another at a normal temperature, the network structure can be sufficiently formed before the dehydration ring closure reaction. Therefore, the effect of suppressing swelling occurring with aggregation of water of absorption under a condition of a high temperature and a high humidity is greater than the effect of the aforementioned polyimide of Japanese Patent Application No. 2002-32924, and the effect of suppressing the drift is also believed to be greater.

FIG. 2 shows an example of a humidity sensor using the humidity sensitive element according to the invention. Reference numeral 1 denotes a substrate that is a silicon substrate or a glass substrate, for example. A corrosion resistant lower electrode 2 of Au, Pt or Cr is deposited in vacuum or sputtered onto the substrate 1 to form a film. The thickness of this film is from about 50 to about 500 nm at this time. Next, patterning is carried out into a desired shape. The patterning method includes a method that forms a mask by using photolithography and then conducts etching and a method that conducts film formation while a metal mask is put on the substrate and forms a film only at desired portions.

Next, polyimide 3 as a humidity sensitive film is formed. The polyimide is generally provided in the form of varnish in which a polyamide acid as a precursor of the polyimide is diluted by a solvent such as N-methylpyrrolidone. Here, a polyamide acid solution as the precursor of the polyimide having the molecular structure of the invention is applied by spin coating, or the like. Thereafter, the polyamide acid solution is heated stepwise at 120° C. for 30 minutes, 200° C. for 60 minutes and 350° C. for 60 minutes, for example, to cause dehydration condensation and hardening. The thickness of the film after hardening is suitably from about 1 to about 5 μm. When the film is too thin, the possibility of short-circuit occurs due to a partial absence of the film resulting from steps on the surface of the base coats and when the film is too thick, diffusion of water absorbed into the polyimide humidity sensitive film is retarded and the response is likely to become slow.

Next, an upper electrode 4 is formed. The upper electrode must have water permeability to achieve quick permeation to the humidity sensitive film of the base besides its role as an electrode having high electric conduction. To satisfy this requirement, an Au electrode is formed as a thin film 3 to 15 nm thick by vacuum sputtering or a porous carbon film is formed by screen printing.

Finally, the film is diced into chips and the intended humidity sensors can be obtained.

This embodiment has been explained regarding the structure in which the polyimide humidity sensitive films are sandwiched by electrodes but the invention is not limited to this construction. For example, a construction in which an insulating film is formed on an insulating substrate or a conductive substrate, a pair of comb-tooth electrodes is formed on this insulating film and a polyimide humidity sensitive film is formed on the former to detect an electrostatic capacitance between the comb-tooth electrodes in the transverse direction, can be used without any problem.

Figure 3:
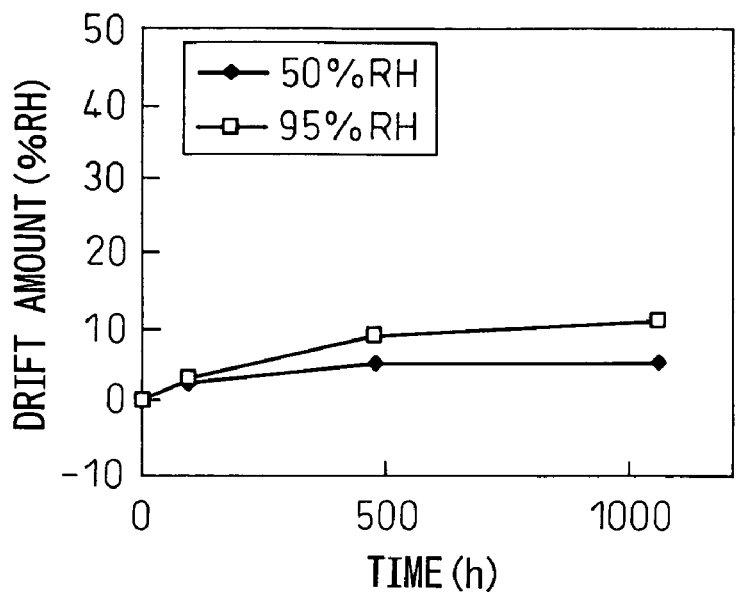
FIG. 3 shows drift characteristics of a humidity sensor constituted by a polyimide humidity sensitive film according to the invention after it is left standing at a high temperature and a high humidity.
Figure 4:
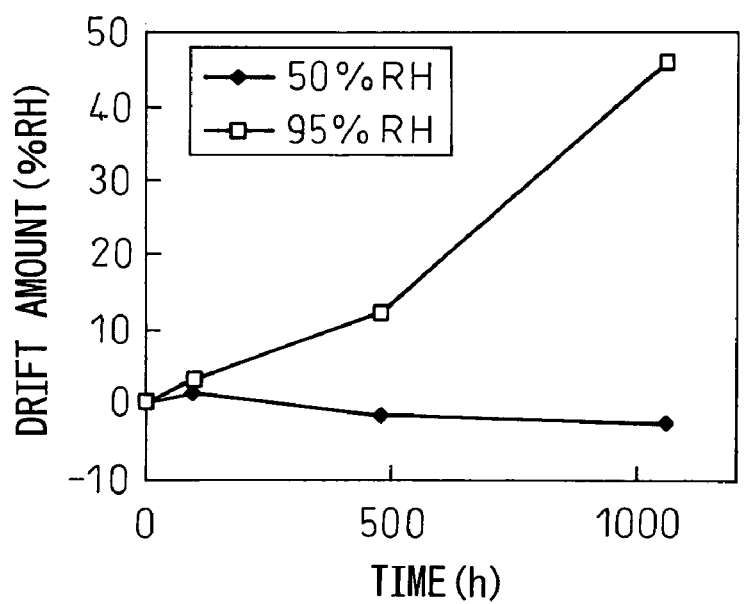
FIG. 4 shows drift characteristic of a humidity sensor constituted by a polyimide humidity sensitive film according to the prior art after it is left standing at a high temperature and a high humidity.

Next, drift characteristics of the humidity sensor constituted by the polyimide humidity sensitive film according to the invention after it is left standing at a high temperature and a high humidity will be explained. After the humidity sensor is left standing for a predetermined time in a high temperature high humidity atmosphere of 65° C. and 90% RH, the electrostatic capacitance of the sensor in an atmosphere of 25° C. and 50% RH or 25° C. and 95% RH is measured. The difference between this value and the electrostatic capacitance value measured before the sensor is left standing in the high temperature high humidity atmosphere is converted to a relative humidity and is used as the drift amount. FIG. 3 shows the result. FIG. 4 shows the change of the humidity sensor using the polyimide according to the prior art after the sensor is left standing in the high temperature and high humidity atmosphere. It can be clearly understood that the humidity sensor using the polyimide of the invention for the humidity sensitive film exhibits a smaller drift after being left standing in the high temperature high humidity atmosphere and has superior characteristics.

The invention provides a humidity sensitive element using the polyimide having the molecular structure capable of forming the network structure in a high density as the humidity sensitive film, and this humidity sensitive element exhibits a small drift after being left standing at a high temperature and a high humidity and has excellent characteristics.

What is claimed is:

1. A humidity sensitive element using polyimide obtained by dehydrating and ring closing a polyamide acid having basic molecular chains whose terminals are interconnected to one another to form a network structure;

wherein said basic molecular chain has a molecular structure expressed by the formula (1):

-[acid component-diamine component]$_n$-acid component-     (1)

(where n represents a number of repetitions representing a degree of polymerization);

wherein the terminals of said basic molecular chain having the molecular structure expressed by the formula (1) are interconnected with one another by using triamine:

-[acid component-diamine component]$_n$-acid component-     (1)

(where n represents a number of repetitions representing a degree of polymerization).

2. A humidity sensitive element according to claim 1, wherein said triamine is 2,4,6-triaminopyridine or 1,3,5-triaminobenzene.

3. A humidity sensitive element according to claim 1, wherein the number of repetitions n is 1 to 30.

4. A humidity sensitive element according to claim 3, wherein the number of repetitions n is 3 to 20.

5. A humidity sensitive element according to claim 1, wherein the acid component in the formula (1) has a molecular structure expressed by the formula (3):

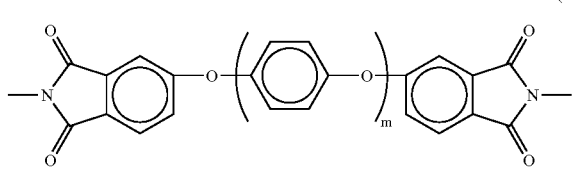
(3)

(where m is an integer of 0 to 5).

6. A humidity sensitive element according to claim 1, wherein the diamine component in the formula (1) has a molecular structure expressed by the formula (4):

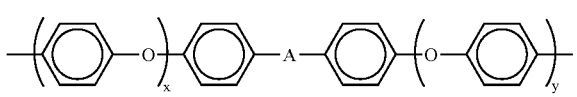
(4)

(where A is a single bond, a polyfluoroalkyl group or a sulfonyl group and each of x and y is an integer of 1 to 5).

7. A humidity sensor using said humidity sensitive element according to claim 1.

8. A humidity sensitive element using polyimide obtained by dehydrating and ring closing a polyamide acid having basic molecular chains whose terminals are interconnected to one another to form a network structure;
wherein said basic molecular chain has a molecular structure expressed by the formula (2):

-[diamine component-acid component]$_n$-diamine component- (2)

(where n represents a number of repetitions representing a degree of polymerization);
wherein the terminals of said basic molecular chains having the molecular chain expressed by the formula (2) are interconnected with one another by using a tricarboxylic acid:

-[diamine component-acid component]$_n$-diamine component- (2)

(where n represents a number of repetitions representing a degree of polymerization).

9. A humidity sensitive element according to claim 8, wherein said tricarboyxlic acid is a trimesic acid or a trimesitic acid.

10. A humidity sensitive element according to claim 8, wherein the number of repetitions is 1 to 30.

11. A humidity sensitive element according to claim 10, wherein the number of repetitions is 3 to 20.

12. A humidity sensitive element according to claim 8, wherein the acid component in the formula (2) has a molecular structure expressed by the formula (3):

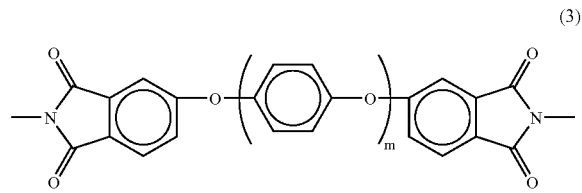
(3)

(where m is an integer of 0 to 5).

13. A humidity sensitive element according to claim 8, wherein the diamine component in the formula (2) has a molecular structure expressed by the formula (4):

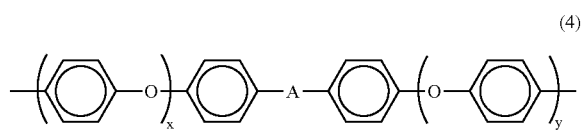
(4)

(where A is a single bond, a polyfluoroalkyl group or a sulfonyl group and each of x and y is an integer of 1 to 5).

* * * * *